United States Patent
Catheline et al.

(10) Patent No.: US 10,368,750 B2
(45) Date of Patent: Aug. 6, 2019

(54) SHEAR WAVE IMAGING METHOD AND INSTALLATION FOR COLLECTING INFORMATION ON A SOFT SOLID

(71) Applicants: Institut National de la Sante et de la Recherche Medicale (INSERM), Paris (FR); Universite Claude Bernard Lyon I, Villeurbanne (FR)

(72) Inventors: Stefan Catheline, Lyons (FR); Jean-Yves Chapelon, Lyons (FR); Remi Souchon, Lyons (FR); Pol Grasland-Mongrain, Lyons (FR); Cyril Lafon, Lyons (FR)

(73) Assignees: INSERM (Institut National de la Santé et de la Recherche Médicale), Paris (FR); Université Claude Bernard Lyon 1, Villeurbanne (FR)

( * ) Notice: Subject to any disclaimer, the term of this patent is extended or adjusted under 35 U.S.C. 154(b) by 882 days.

(21) Appl. No.: 14/903,876

(22) PCT Filed: Jul. 10, 2014

(86) PCT No.: PCT/EP2014/064794
§ 371 (c)(1),
(2) Date: Jan. 8, 2016

(87) PCT Pub. No.: WO2015/004224
PCT Pub. Date: Jan. 15, 2015

(65) Prior Publication Data
US 2016/0367143 A1    Dec. 22, 2016

(30) Foreign Application Priority Data
Jul. 11, 2013 (EP) .................................. 13305987

(51) Int. Cl.
*A61B 5/00* (2006.01)
*A61B 8/08* (2006.01)
(Continued)

(52) U.S. Cl.
CPC .............. *A61B 5/0051* (2013.01); *A61B 5/05* (2013.01); *A61B 5/055* (2013.01); *A61B 5/0536* (2013.01);
(Continued)

(58) Field of Classification Search
CPC ....... A61B 5/0051; A61B 5/05; A61B 5/0536; A61B 5/055; A61B 8/485; G01R 33/56358
See application file for complete search history.

(56) References Cited

U.S. PATENT DOCUMENTS

| | | | | |
|---|---|---|---|---|
| 6,583,624 B1* | 6/2003 | Muthupillai | ..... | G01R 33/56308 324/306 |
| 6,704,594 B1* | 3/2004 | Blank | ................ | G01R 33/3808 128/899 |

(Continued)

FOREIGN PATENT DOCUMENTS

| | | |
|---|---|---|
| JP | 2005304898 A | 4/2005 |
| WO | 2005/102161 A1 | 11/2005 |

*Primary Examiner* — Dixomara Vargas
(74) *Attorney, Agent, or Firm* — W & C IP

(57) ABSTRACT

This shear wave imaging method, for collecting information on a target region (R) of a soft solid (S), comprises at least the steps a) of generating at least one shear wave (SW) in the target region, and b) of detecting a propagation pattern of the shear wave in the target region. Step a) is realized by applying to particles of the target region (R) some Lorentz forces resulting from an electric field (E) and from a magnetic field (B). At least one of the electric field (E) and the magnetic field (B) is variable in time, with a central frequency ($f_o$) between 1 Hz and 10 kHz. Alternatively, both the electric and magnetic fields (E, B) are variable in time, (Continued)

with a central difference frequency ($\Delta f_o$) between 1 Hz and 10 kHz. The shear wave imaging installation comprises a first system (4, 7) for generating at least one shear wave (SW) in the target region (R) and a second system (10) for detecting a propagation pattern of the shear wave. The first system includes first means (4) to apply an electric field (E) through the target region (R) and second means (7) to apply a magnetic field (B) through the target region. The first and second means are configured to apply to particles of the target region some Lorentz forces resulting from the electric field (E) and the magnetic field (B), where at least one of these fields is a quantity variable in time, with a central frequency ($f_o$) between 1 Hz and 10 kHz, or both fields are quantities variable in time, with a central difference frequency ($\Delta f_o$) between 1 Hz and 10 kHz.

17 Claims, 3 Drawing Sheets

(51) Int. Cl.
*A61B 5/05* (2006.01)
*A61B 5/053* (2006.01)
*G01R 33/563* (2006.01)
*A61B 5/055* (2006.01)

(52) U.S. Cl.
CPC ........ *A61B 8/485* (2013.01); *G01R 33/56358* (2013.01)

(56) References Cited

U.S. PATENT DOCUMENTS

| | | | |
|---|---|---|---|
| 6,770,033 B1 | 8/2004 | Fink et al. | |
| 8,253,415 B2* | 8/2012 | Umeda | G01R 33/485 324/307 |
| 8,791,698 B2* | 7/2014 | Umeda | G01R 33/485 324/307 |
| 10,101,495 B2* | 10/2018 | Li | G01V 11/007 |
| 2006/0152219 A1 | 7/2006 | Bieri et al. | |
| 2006/0253015 A1* | 11/2006 | Nezafat | G01R 33/5635 600/410 |
| 2007/0151344 A1* | 7/2007 | Meethal | G01N 29/2412 73/649 |
| 2010/0030120 A1* | 2/2010 | Graham | G01R 33/28 601/78 |
| 2011/0316537 A1* | 12/2011 | Umeda | G01R 33/485 324/310 |
| 2016/0116553 A1* | 4/2016 | Kim | G01R 33/032 324/305 |
| 2017/0261642 A1* | 9/2017 | Li | G01V 11/007 |
| 2017/0352435 A1* | 12/2017 | Wong | H05H 1/10 |
| 2018/0322962 A1* | 11/2018 | Wong | H05H 1/10 |
| 2019/0057782 A1* | 2/2019 | Wong | H05H 1/16 |

* cited by examiner

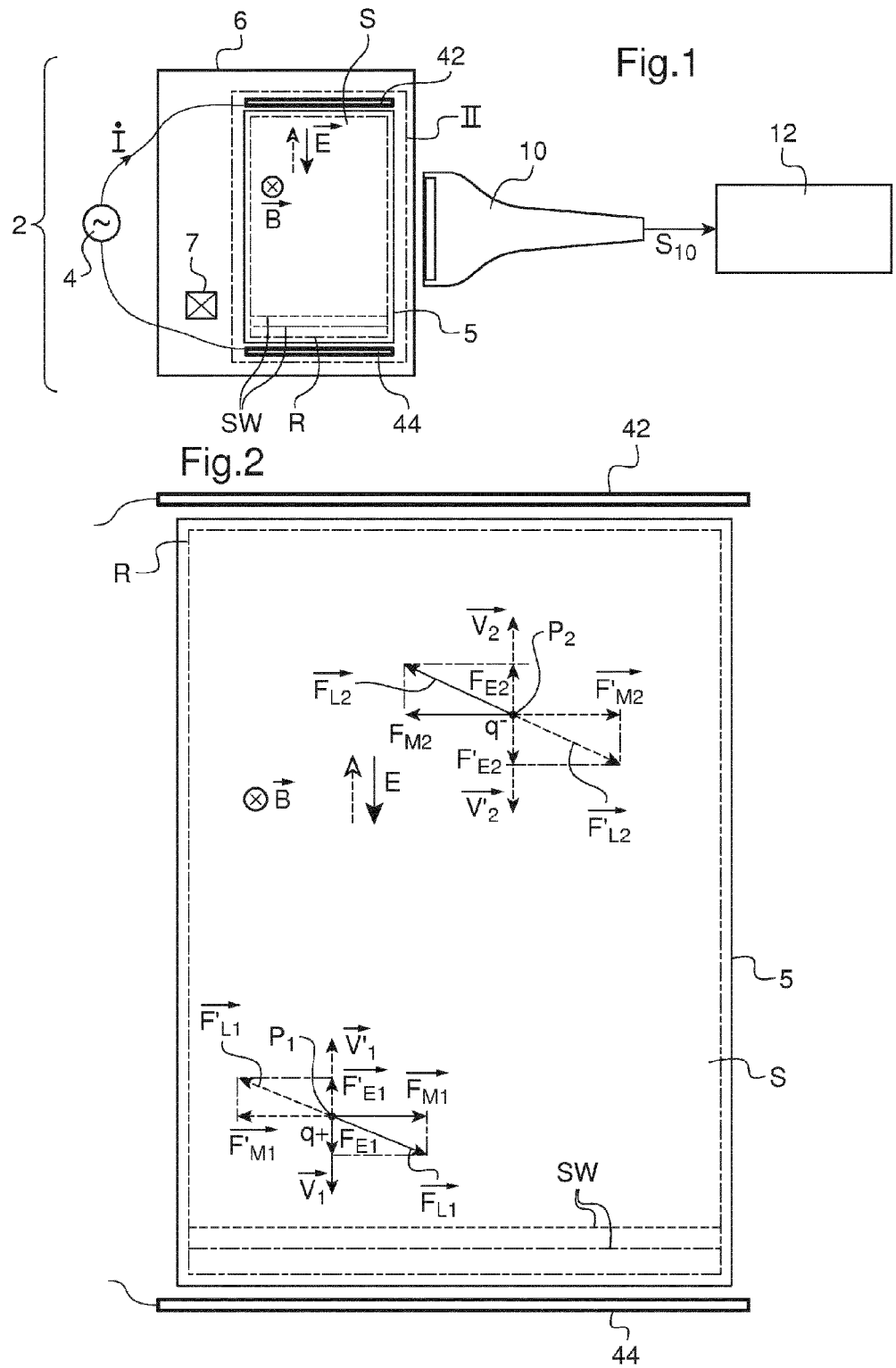

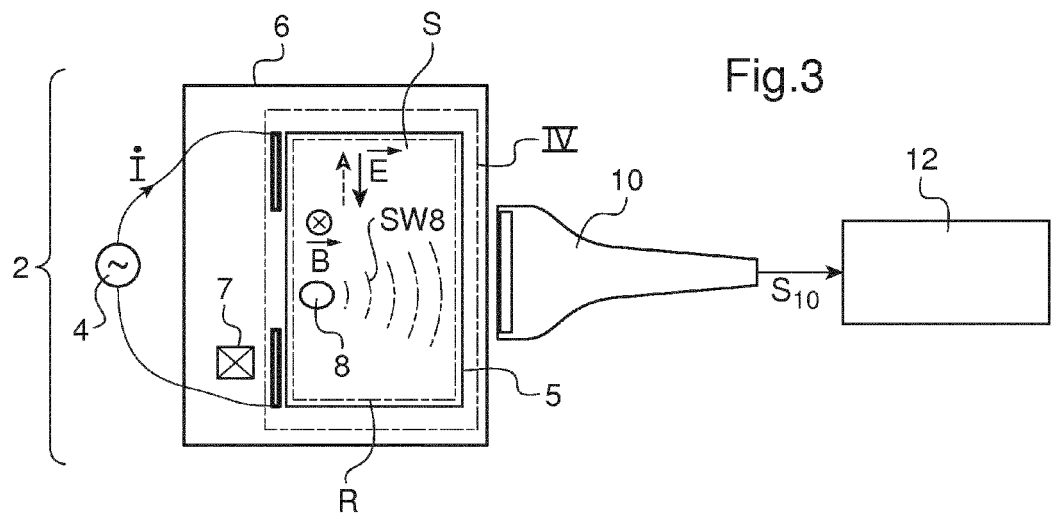
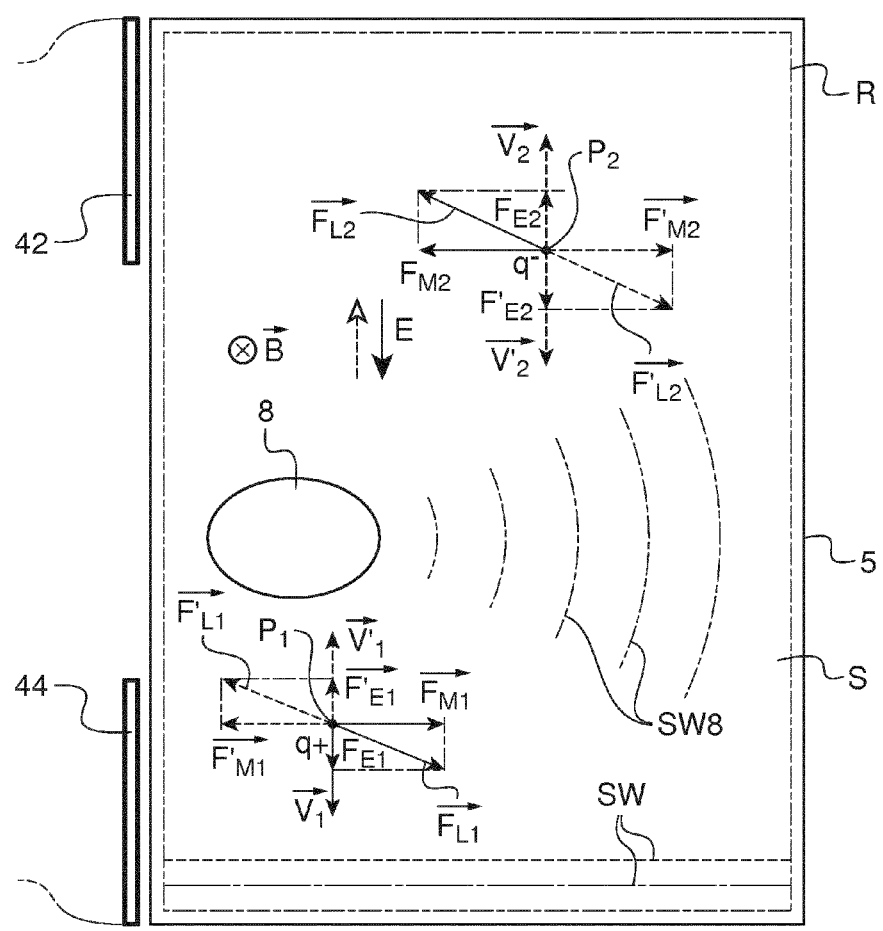

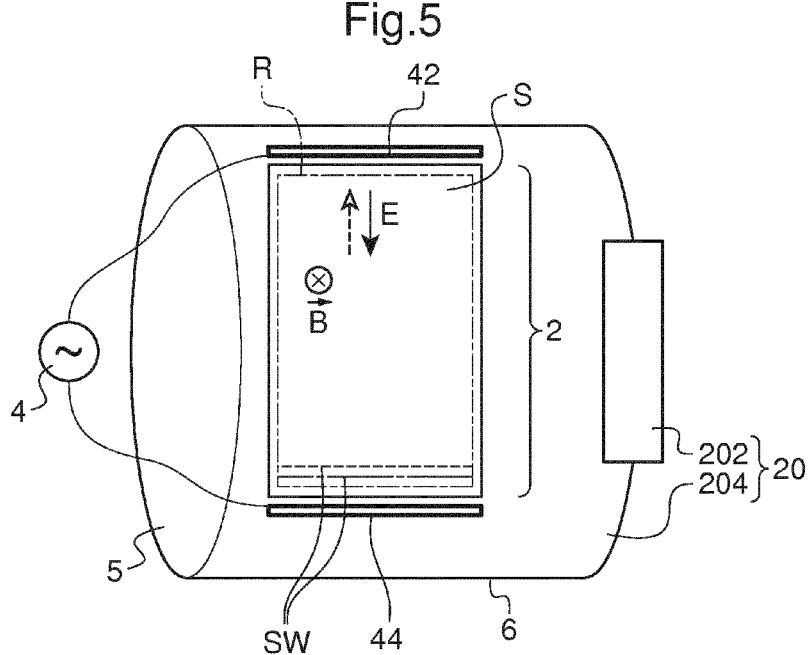
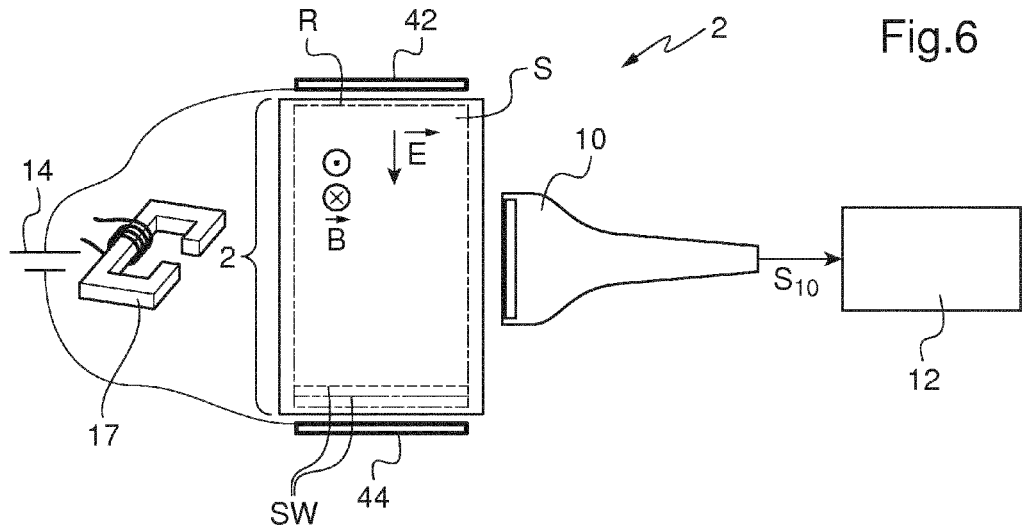

SHEAR WAVE IMAGING METHOD AND INSTALLATION FOR COLLECTING INFORMATION ON A SOFT SOLID

TECHNICAL FIELD OF THE INVENTION

This invention relates to a shear wave imaging method for collecting information on a target region of a soft solid. This invention also relates to a shear wave imaging installation for performing such a method.

In the meaning of the present invention, a soft solid is an organic tissue which can have an animal or vegetal origin. For instance, such a soft solid can be an organ of a human body, of an animal body or of a vegetable. A soft solid can also be an aliment, e.g. cheese, or a non metallic part of a prosthesis, made of a natural or synthetic material.

BACKGROUND OF THE INVENTION

Shear wave elastography has been known for several years as an efficient technique for detecting an inhomogeneity of elasticity in a soft solid, such as a tumor. This technique is based on the detection of shear waves propagation speed. Such a detection can be based on an ultrasonic technology or on a magnetic resonance imaging (MRI) technology.

In a soft solid, shear waves propagate at a speed in the range of 1 to several meters per second (m/s) and this speed can be used to characterize a target region of a soft solid since the speed pattern of these waves allows generating images representative of the shear elastic modulus. This shear elastic modulus approximately corresponds to the elasticity which can be sensed by palpation and is ranging from a few hundred Pa to a few thousand kPa. This is different from an approach based on the propagation of compression waves which propagate at a much higher speed, in the range of 1500 m/s, in a soft solid. The repartition of the compression waves in such a solid is representative of the compression elastic modulus of the tissue, typically in the order of 2.4 GPa, six orders of magnitude bigger than the shear elastic modulus. This is why biological tissues are generally considered not to be compressible. Thus, a detection method based on the propagation of compression waves cannot be considered as an elastography method.

In the field of elastography, it is known from U.S. Pat. No. 6,770,033 to use a loudspeaker controlled by a micro computer so as to apply an excitation, in the form of a low-frequency pulse, to the surface of a soft solid. In order to use the device of U.S. Pat. No. 6,770,033, one must manipulate, with one hand, the loudspeaker and, with the other hand, a sensor which is supposed to collect information with respect to the propagation of shear waves generated in the tissue. This is tedious and requires a high expertise.

U.S. Pat. No. 5,606,971 discloses a method for shear wave elasticity imaging where shear waves are generated in a focus zone of a piezo-electric transducer inside soft solids to be studied. This transducer has a double function: it creates the shear waves and it detects them. With this approach, shear waves can be generated in a target zone close to the transducer array. However, this technique is difficult to implement when the target zone is far from the transducer array, for instance in deep organs. Actually, the ultrasound energy deposition quickly decreases with depth, and under such circumstances, the ultrasound radiation force cannot create effective shear waves propagation.

On the other hand, US-A-2009/018432 discloses a method for imaging with magnetic induction, where one uses a magnetic pulsed stimulation with a duration in the order of one microsecond (µs). In other words, the excitation frequency of the magnetic stimulation is in the range of 1 MHz, which generates compression waves, but no shear waves. It is known that shear waves are strongly attenuated and cannot propagate in tissues at such a frequency. A key aspect of the teachings of US-A-2009/018432 is that the precision of the resolution depends on the frequency used for the magnetic stimulation. Under such circumstances, the method described in this document relies on the use of high frequency excitation, in order to obtain a satisfactory resolution. On the contrary, elastography requires low vibration frequencies to induce shear waves. Therefore the technology of US-A-2009/018432 is not adapted to shear wave elastography.

U.S. Pat. No. 6,583,624 discloses a method where a voltage applied to a subject material is used to produce shear waves and an IRM technique is used to detect the shear waves. A magnetic field is used for the IRM detection, but it does not participate to the shear waves generation.

US-A-2006/0152219 discloses a method where either a piezoelectric actuator, alternating currents or an alternating magnetic field is/are used to input mechanical motions to spins within a sample.

In these two last prior art documents, one relies on a single electric phenomenon to move some particles and, where a magnetic field is applied for the IRM detection, it is not used to generate shear waves. Thus, shear waves generation in deep target regions is also difficult to obtain with these techniques.

SUMMARY OF THE INVENTION

The invention aims at solving the problems of known elastography methods with a new method which is efficient to generate shear waves, even in deep target regions of a soft solid. More generally speaking, the invention aims at providing a shear wave imaging method which is easy to implement and can be used for elastography or electric tomography.

To this end, the invention concerns a shear wave imaging method for collecting information on a target region of a soft solid, this method comprising at least the following steps:
  a) generating at least one shear wave in the target region,
  b) detecting a propagation pattern of the at least one shear wave in the target region,
  This method is characterized in that
  step a) is realized by applying to particles of the target region some Lorentz forces resulting from an electric field and from a magnetic field,
  at least one of the electric field and magnetic field is variable in time, with a central frequency between 1 Hz and 10 kHz or both the electric field and the magnetic field are variable in time, with a central difference frequency between 1 Hz and 10 kHz.

Thanks to the invention, one uses Lorentz forces induced both by the electric field and by the magnetic field to generate one or several shear waves in the soft solid to be studied. This is possible thanks to the conjunction of the electric field and the magnetic field which each contributes to a portion of the Lorentz forces applied to an electrically loaded particle, according to the following equation:

$$\vec{F}_L = q\vec{E} + q\cdot\vec{V} \wedge \vec{B} = \vec{F}_E + \vec{F}_M \qquad \text{(equation 1)}$$

where $\vec{F}_L$ is the Lorentz force applied on a particle
q is the electric load of the particle
· denotes multiplying two terms
$\vec{E}$ is the electric field applied to the particle
$\vec{V}$ is the velocity of the particle
∧ denotes the vectorial product
$\vec{B}$ is the magnetic field applied to the particle
$\vec{F}_E$ is the electric force applied to the particle, also called Coulomb force, and equals q $\vec{E}$
$\vec{F}_M$ is the magnetic force applied to the particle, also called Laplace force, and equals q·$\vec{V}$∧$\vec{B}$ Thus, Lorentz forces applied to a particle of the target region include Coulomb forces and Laplace forces.

Since at least one of the electric and magnetic fields is variable, the Lorentz force applied to a particle is also variable, which implies that a wave is generated. When two variable fields are used, their central difference frequency also induces a variable Lorentz force. Since the central frequency of the variable field or the central difference frequency is relatively low, below 10 kHz, the variable Lorentz force generates a shear wave. The propagation speed of this shear wave can be measured to determine the shear elastic modulus of a soft solid, leading to an elastography method. This enables to draw a map of the shear elastic modulus of the soft solid. Alternatively or in addition, it is also possible to detect, on the basis of the shear wave propagation pattern, the source of each shear wave which can be considered to correspond to an elastic inhomogeneity. In case of an electrically heterogeneous soft solid, the method of the invention enables to draw a map of the electric conductivity of the soft solid.

According to further aspects of the invention which are advantageous but not compulsory, the method might incorporate one or several of the following features, taken in any technically admissible configuration:

- During step a), the electric field is variable in time and the magnetic field is constant in time. Alternatively, during step a), the magnetic field is variable in time and the electric field is constant in time. According to another alternative, during step a), both the electric field and the magnetic field are variable in time, at frequencies between 1 Hz and 10 kHz, or both the electric field and the magnetic field are variable in time at high frequencies, with a central difference frequency between 1 Hz and 10 kHz.
- The central frequency of the variable field or the central difference frequency is between 5 and 1000 Hz, preferably between 50 and 150 Hz.
- The electric field is generated by two electrodes located on either sides, on one side or within the soft solid and connected to a source of electric current with an intensity between 1 µA and 1 A. Alternatively, the electric field is generated by a second magnetic field which is variable in time.
- The soft solid is a biological tissue, of human, animal or vegetal origin, preferably an organ. Alternatively, the soft solid is an artificial medium.
- During step b), measurement of the shear waves propagation speed occurs via a sensor assembly based on ultrasound technology. Alternatively, measurement of the shear waves propagation speed can occur via a sensor assembly based on MRI technology. In such a case, the magnetic field used during step a) might be generated by the sensor assembly based on MRI technology.
- According to another approach, during step b), one detects a source of the at least one shear wave.

The invention also concerns a shear wave imaging installation which can be used to perform the method mentioned here-above and, more specifically, an installation for collecting information on a target region of a soft solid, this installation comprising a first system for generating at least one shear wave in the target region and a second system for detecting a propagation pattern of the at least one shear wave. This installation is characterized in that the first system includes:

- first means to apply an electric field through the target region and
- second means to apply a magnetic field through the target region, and in that the first and the second means are configured to apply to particles of the target region some Lorentz forces resulting from the electric field and the magnetic field where at least one of these fields is a quantity variable in time, with a central frequency between 1 Hz and 10 kHz, or both the electric and magnetic fields are quantities variable in time, with a central difference frequency between 1 Hz and 10 kHz.

According to an advantageous aspect of the invention, the first means include a set of electrodes installed on either sides, on one side or within the soft solid and connected to a source of electric current, with an intensity between 1 µA and 1 A.

BRIEF DESCRIPTION OF THE DRAWINGS

The invention will be better understood on the basis of the following description which is given in correspondence with the appended figures and as an illustrative example, without restricting the object of the invention. In the annexed figures:

FIG. 1 is a schematic representation of an installation according to a first embodiment of the invention;

FIG. 2 is a view at a larger scale of detail II on FIG. 1;

FIG. 3 is a schematic representation similar to FIG. 1, for an installation according to a second embodiment of the invention;

FIG. 4 is a view at a larger scale of detail IV on FIG. 3;

FIG. 5 is a schematic representation similar to FIG. 1, for an installation according to a third embodiment of the invention; and FIG. 6 is a schematic representation similar to FIG. 1, for an installation according to a fourth embodiment of the invention.

DETAILED DESCRIPTION OF SOME EMBODIMENTS

The installation 2 represented on FIGS. 1 and 2 includes an alternative current generator 4 which is connected to a first electrode 42 and to a second electrode 44 located on either sides of an electrically conductive soft solid S housed in a box 5. Box 5 is optional and can be omitted if soft solid S stands on its own. Soft solid S can be a portion of an animal body, such as a muscle. In such a case, no box 5 is needed. Soft solid S is considered to be electrically conductive insofar as its conductivity is between $10^3$ and 1 Siemens per meter (S/m) for frequencies between 1 Hz and 10 kHz. In other words, at least some particles of soft solid S are electrically loaded, with a positive or negative charge $q^+$ or $q^-$.

One considers a region R of soft solid S to be studied by elastography. In the example of FIGS. 1 and 2, region R corresponds almost to the totality of solid S located in box 5, between electrodes 42 and 44. Alternatively, region R can correspond to a smaller portion of solid S.

Since an alternative current I is applied to electrodes 42 and 44, an alternative electric field $\vec{E}$ is generated between these electrodes, across region R of soft solid S.

Generator 4 delivers a current with an amplitude I equal to 100 mA, with a sinusoidal shape and a frequency f equal to 100 Hz.

In practice, amplitude I of the current can be selected between 1 μA and 1 A and frequency f can vary in a range between 1 Hz and 10 kHz. Preferably, frequency f is chosen in the range 5 to 1000 Hz, most preferably in the range 50 to 150 Hz, whereas the value of 100 Hz gives good experimental results.

One defines the central frequency $f_o$ of a variable signal as the arithmetic mean value of the Fourier transform of this signal. Such a definition is known, e.g., from J. T. Taylor and Q. Huang in *CRC Handbook of electrical filters* (1997).

Frequency f can be a central frequency $f_o$ in the sense that any modulated signal can be used for the electric field E. Any wave or signal mixing that result in a central frequency as mentioned here-above is suitable for the methods and installations of the invention.

In the present example, as current I delivered by generator 4 is sinusoidal, electric field $\vec{E}$ is sinusoidal, with the same frequency f, and the central frequency $f_o$ of electric field $\vec{E}$ equals the central frequency of the current delivered by generator 4.

Alternatively, the current delivered by generator 4 is not sinusoidal but has the form of a square wave or of one or several picks. In such a case, central frequency $f_o$ can be calculated via a Fourier transform, as explained here-above.

Region R of soft solid S is also subjected to a constant or permanent magnetic field $\vec{B}$. This permanent magnetic field $\vec{B}$ is generated across soft solid S by a permanent magnet 7. Alternatively, one can use an electromagnet instead of permanent magnet in order to generate magnetic field $\vec{B}$. The field strength of magnetic field of $\vec{B}$ is between 10 mT and 10 T. The direction of magnetic field $\vec{B}$ is perpendicular to the plane of FIG. 1, that is perpendicular to electric field $\vec{E}$. In this example, magnetic field $\vec{B}$ is directed away from the viewer of FIGS. 1 and 2.

Reference 6 denotes a closed envelope, preferably shielded against magnetic perturbations, inside which magnetic field $\vec{B}$ is generated.

Coming now to FIG. 2, one considers a particle $P_1$ of soft solid S which is loaded with a positive electric charge $q^+$. One considers the case where electric field $\vec{E}$ is directed from electrode 42 towards electrode 44, as shown by the arrow in solid line on FIG. 2. Because of electric field $\vec{E}$, particle $P_1$ is subjected to an electric force $\vec{F}_{E1}$ which equals $q^+ \cdot \vec{E}$ and is parallel to electric field $\vec{E}$ and oriented in the same direction because electric charge $q^+$ is positive. This corresponds to the first part of equation 1.

Under the effect of this electric force, particle $P_1$ moves in the same direction and has a velocity $\vec{V}_1$ oriented in the same direction. Because of this velocity $\vec{V}_1$ and of the second part of equation 1, particle $P_1$ is also subjected to a magnetic force $\vec{F}_{M1}$ which equals $q^+ \cdot \vec{V}_1 \wedge \vec{B}$ and which is oriented to the right on FIG. 2. Thus, particle $P_1$ is subjected to a Lorentz force $\vec{F}_{L1}$ oriented to the right and towards electrode 44 on FIG. 2.

When the polarity between electrodes 42 and 44 is inverted, then electric field $\vec{E}$ is oriented as shown by the arrow in dashed line on FIG. 2 and, for the same reasons as explained previously, particle P is subjected to a Lorentz force $\vec{F'}_{L1}$ which is the sum of an electric force $\vec{F'}_{E1}$ and a magnetic force $\vec{F'}_{M1}$ respectively oriented in opposite directions to forces $\vec{F}_{E1}$ and $\vec{F}_{M1}$.

$\vec{F'}_{E1}$ equals $q^+ \cdot \vec{E}$ and $\vec{F'}_{L1}$ equals $q^+ \cdot \vec{V'}_1 \wedge \vec{B}$ where $\vec{V'}_1$ is the velocity of particle $P_1$ under the effect of electric field $\vec{E}$ oriented towards electrode 42.

Thus, because of the fact that electric field $\vec{E}$ is variable in time, particle $P_1$ is subjected to alternative Lorentz forces $\vec{F}_{L1}$ and $\vec{F'}_{L1}$, which generates shear waves as shown by axis lines SW at the bottom of FIG. 2.

If one considers another particle $P_2$ with a negative electric charge $q^-$ as represented on top of FIG. 2, then the force distribution will be reversed to the force distribution for particle $P_1$. Nevertheless, this particle $P_2$ will also be subjected to alternative Lorentz forces $\vec{F}_{L2}$ and $\vec{F'}_{L2}$. This will also contribute to the shear wave generation represented by axis lines SW at the bottom of FIG. 2.

In summary, positively loaded particles $P_1$ and negatively loaded particles $P_2$ of soft solid S have roughly the same behavior and <<shake>> because of alternatively changing Lorentz forces, which generates shear waves SW in soft solid S.

As explained here-above, the propagation speed of the shear waves SW can be considered as representative of the shear elastic modulus of soft solid S in region R, irrespective of whether or not the region is elastically homogeneous.

Installation 2 also includes an ultrasonic probe 10 which can be of any known type, e.g. of the type mentioned in U.S. Pat. No. 6,770,033. This probe 10 is connected to an ultrasound scanner 12 which is provided with a speckle tracking module, so that, as known in the art, this scanner is capable of measuring a propagation speed of shear waves SW within region R.

An elastography method implemented with installation 2 is now described: first, one defines target region R of soft solid S as the portion of this soft solid located between electrodes 42 and 44, within envelope 6. When the generator 4 is actuated, this region R is subjected to electric field $\vec{E}$ and magnetic field $\vec{B}$. As mentioned here-above, this results in submitting positive and negative particles $P_1$ and $P_2$ to variable Lorentz forces, which generates shear waves SW in the target region R. Depending on the distribution and strength of electric field $\vec{E}$ and magnetic field $\vec{B}$, one or several shear waves is/are generated. This or these shear waves can then be detected by ultrasonic probe 10 which sends a corresponding electronic signal $S_{10}$ to ultrasound scanner 12. The speckle tracking module of ultrasound scanner 12 detects the propagation speed of shear waves SW in ant direction.

If region R is elastically homogeneous, the propagation speed of shear waves SW within region R is constant and a measure of this speed allows to determine, via the speckle tracking module of ultrasound scanner 12, the shear elastic modulus of sift solid S within this region.

If region R is elastically heterogeneous, the different propagation speeds of shear waves SW with region R can be measured and a map of the corresponding shear elastic modulus values, within region R, can be established.

Thus, the method of the invention is an elastography method and it is very efficient to detect any elasticity inhomogeneity, even in a deep region of tissue R, which is relatively far away from its boundaries considered as the portion of tissue R close to electrodes 42 and 44.

The frequency used for working ultrasonic probe 10 is between 100 kHz and 100 MHz, preferably between 2 MHz and 20 MHz, with a pulse repetition frequency between 10 Hz and 100 kHz, preferably between 1 kHz and 5 kHz.

In the second, third and fourth embodiments of the invention respectively represented on FIGS. 3 to 6, the same pieces of equipment as in the first embodiment have the same reference numbers. Here-after, only the differences with the first embodiment are listed.

In the embodiment of FIGS. 3 and 4, electrodes 42 and 44 are located on one side of soft solid S.

If an electrical impedance inhomogeneity 8 is present in region R of soft solid S, then the behavior of its positive and negative particles under the effect of Lorentz forces is different from the behavior of the positive and negative particles $P_1$ and $P_2$ of the rest of tissue T. Shear waves SW8 generated in the region of this inhomogeneity 8 have a different pattern than shear waves SW, as shown in FIG. 4.

According to another method of the invention, it is possible to locate, thanks to ultrasound scanner 12, the source region of shear waves SW8, which can be identified as an impedance inhomogeneity. On this basis, it is possible to draw a map or "tomographic image" of the electrical conductivity of soft solid S within region R. Thus, an electric tomography method is implemented.

If soft solid S is elastically and electrically heterogeneous, then a combination of the elastography and electric tomography methods mentioned here-above in reference to FIGS. 2 and 4 can be implemented.

In the embodiment of FIG. 5, one uses a Magnetic resonance imaging (MRI) system assembly 20 to measure shear waves propagation speed in the target region R of a soft solid S. MRI assembly 20 includes a MRI probe 202 and an MRI magnetic field generator 204, which generates a permanent or constant magnetic field $\vec{B}$.

An electric field $\vec{E}$ is generated as in the first embodiment, by a sinusoidal current generator 4 which is connected to electrodes 42 and 44.

In this embodiment, one takes advantage from the fact that a permanent magnetic field is generated for MRI subassembly 20, by field generator 204. This permanent magnetic field is used as the constant magnetic field $\vec{B}$ of the first embodiment to generate the shear waves, in conjunction with electric field $\vec{E}$.

With this embodiment, one can implement an elastography method, similar to the one mentioned in reference to FIG. 2, and/or an electric tomography method, similar to the one mentioned in reference to FIG. 4.

In the embodiment of FIG. 6, a variable magnetic field $\vec{B}$ is generated, with a central frequency $f_o$ between 1 Hz and 10 kHz, preferably in the same range as the one mentioned for the electric field $\vec{E}$ of the first embodiment. The strength of this variable magnetic field is between 10 mT and 10 T.

The pulse shape of the magnetic field $\vec{B}$ can be sinusoidal, square or have any arbitrary wave form. This variable magnetic field $\vec{B}$ is created by an electro-magnet 17.

A static or constant electric field $\vec{E}$ is generated between two electrodes 42 and 44 via a generator of DC current 14. The static electrical current generated by generator 14 can have an intensity between 1 μA and 1 A.

As mentioned with respect to the first embodiment, the positive and negative particles of a region R of soft solid S located between electrodes 42 and 44 are subjected to variable Lorentz forces, which generates shear waves.

An ultrasonic probe 10 is connected to an ultrasound scanner 12 and measures the propagation speed of the shear waves, as in the first embodiment, in order to implement an elastography method. Alternatively or in addition, an electric tomography method can be implemented on the basis of the detection of sources of shear waves corresponding to impedance inhomogeneities. Alternatively, a MRI subassembly can be used, instead of ultrasonic probe 10 in the fourth embodiment.

According to an alternative embodiment which is not represented on the figures, one can use two variable fields, namely a variable electric field $\vec{E}$ and a variable magnetic field $\vec{B}$, each of them having a central frequency $f_o$ between 1 Hz and 10 kHz. According to still another alternative embodiment which is not represented, each one of electric E and magnetic field $\vec{B}$ is a high frequency field, preferably a field modulated in amplitude, frequency and/or phase. In such a case, the respective frequencies of these fields, which can be as high as several MHz, are chosen so that their central difference frequency $\Delta f_o$, computed on the basis of their difference frequency $\Delta f$, is in the range 1-10 kHz, preferably 5 to 1000 Hz, more preferably between 50 and 150 Hz.

According to another non represented alternative embodiment, the electrical field $\vec{E}$ can be generated by a second magnetic field $\vec{B}'$, because a variable magnetic field generates an electrical field, leading to eddy currents in the soft solid S.

According to still another embodiment which is not represented, electrodes 42 and 44 can be installed within region R, instead of on one side, either sides or around this solid for the embodiments shown on the figures.

The invention is explained here-above when fields $\vec{E}$ and $\vec{B}$ are perpendicular to each other. It can also be implemented with non perpendicular fields $\vec{E}$ and $\vec{B}$, provided that they are not collinear.

Irrespective of the actual method used to generate the shear waves SW, as explained here-above, the ultrasonic probes 10 or the MRI subassembly 20 can detect an abnormality, such as a cancerous tumor, as an inhomogeneity 8. In a zone of target region R where such a cancerous tumor exists, soft solid S is not as soft as in the other zone, so that shear waves tend to propagate quicker than in the other zones. This difference in shear waves propagation speed can then be interpreted as an indication that a cancerous tumor is present or might be present in this region.

The invention is not limited to the detection of tumors in organs. It can be used to characterize different types of soft solids, animal or vegetal soft solids and soft material in cosmetic or food industry. The invention can also be used to characterize non metallic portions of prostheses.

In order to increase the accuracy of the method of the invention, metallic particles can be injected in the soft solid. Alternatively, a conductive liquid, such as salty water, can be injected in the bladder of a patient in order to facilitate generation of shear waves in the prostate, the stomach, the liver or the pancreas.

The invention can be implemented at a macroscopic level, as explained here-above, and also at a microscopic level. In particular, a biological cell can be considered as soft solid for implementing the method of the invention.

The embodiments and variants considered here-above can be combined in order to generate new embodiments of the invention.

The invention claimed is:

1. Shear wave imaging method for collecting information on a target region of a soft solid, the method comprising at least the following steps:
   a) generating at least one shear wave in the target region,
   b) detecting a propagation pattern of the at least one shear wave in the target region
characterized in that
   step a) is realized by applying to particles of the target region some Lorentz forces resulting from an electric field and from a magnetic field,
   at least one of the electric field and the magnetic field is variable in time, with a central frequency between 1 Hz and 10 kHz or both the electric and magnetic fields are variable in time, with a central difference frequency between 1 Hz and 10 kHz.

2. The method according to claim 1, wherein during step a), a first one of the electric field and the magnetic field is variable in time and the second one of the electric field and the magnetic field is constant in time.

3. The method according to claim 2, wherein during step a), the electric field is variable in time and the magnetic field is constant in time.

4. The method according to claim 2, wherein during step a), the magnetic field is variable in time and the electric field is constant in time.

5. The method according to claim 1, wherein during step a), both the electric field and the magnetic field are variable in time, at frequencies between 1 and 10 kHz, or both the electric field and the magnetic field are variable in time at high frequencies, with a central difference frequency between 1 Hz and 10 kHz.

6. The method according to claim 1, wherein the central frequency of the variable field or the central difference frequency is between 5 and 1000 Hz.

7. The method according to claim 1, wherein the electric field is generated by two electrodes located on both sides, on one side or within the soft solid and connected to a source of electric current with an intensity between 1 µA and 1 A.

8. The method according to claim 1, wherein the electric field is generated by a second magnetic field, variable in time.

9. The method according to claim 1, wherein the soft solid is a biological tissue of human, animal or vegetal origin, preferably an organ, or an artificial medium.

10. The method according to claim 1, wherein during step b), measurement of the shear wave propagation speed occurs via a sensor assembly based on ultrasound technology.

11. The method according to claim 1, wherein during step b), measurement of the shear wave propagation speed occurs via a sensor assembly based on magnetic resonance imaging (MRI) technology.

12. The method according to claim 11, wherein the magnetic field used during step a) is generated by the sensor assembly based on magnetic resonance imaging (MRI) technology.

13. The method according to claim 1, wherein during step b) a source of the at least one shear wave is detected.

14. Shear wave imaging installation for collecting information of a target region of a soft solid, said shear wave imaging installation comprising:
   a first system for generating at least one shear wave in the target region
   a second system for detecting a propagation pattern of the at least one shear wave
characterized in that the first system includes
   first means to apply an electric field through the target region and
   second means to apply a magnetic field through the target region and in that the first and second means are configured to apply to particles of the target region Lorentz forces resulting from the electric field and the magnetic field, where at least one of the electric field and the magnetic field is a quantity variable in time, with a central frequency ($f_o$) between 1 Hz and 10 kHz, or both the electric and magnetic fields are quantities variable in time, with a central difference frequency between 1 Hz and 10 kHz.

15. The installation according to claim 14, wherein the first means includes a set of electrodes installed on both sides, on one side or within the soft solid and connected to a source of electric current with an intensity between 1 µa and 1 A.

16. The method of claim 6, wherein the central difference frequency is between 50 and 150 Hz.

17. The method of claim 9, wherein the biological tissue is an organ.

* * * * *